United States Patent [19]

Ory et al.

[11] 4,141,349
[45] Feb. 27, 1979

[54] PROCESS AND DEVICE FOR THE IN VIVO MEASUREMENT OF BONE CONSOLIDATION

[75] Inventors: Jean-Marie Ory; Jacques Hummer, both of Nancy (Meurthe-et-Moselle), France

[73] Assignee: Agence Nationale de Valorisation de la Recherche (ANVAR), Neuilly sur Seine (Hauts-de-Seine), France

[21] Appl. No.: 738,287

[22] Filed: Nov. 3, 1976

[30] Foreign Application Priority Data

Nov. 4, 1975 [FR] France .................. 75 33713

[51] Int. Cl.$^2$ .............................................. A61B 5/00
[52] U.S. Cl. ................................. 128/2 S; 128/2 R; 73/768; 128/2.1 A
[58] Field of Search ................ 128/2 R, 2.1 R, 2 S, 128/92 B, 92 G, 2 P, 2.1 A, 419 F, 82.1; 73/88.5 R, 172, 88 R; 340/177 VA

[56] References Cited

U.S. PATENT DOCUMENTS

| 3,218,638 | 11/1965 | Honig ........................... 128/2.1 R |
| 3,229,684 | 1/1966 | Nagumo et al. ................. 128/2 P |
| 3,273,559 | 9/1966 | Evans ............................ 128/2 S |
| 3,534,728 | 10/1970 | Barrows ........................ 128/2.1 A |
| 3,757,770 | 9/1973 | Brayshaw et al. ............. 128/2 R |
| 3,883,954 | 5/1975 | Simmering et al. ............ 128/2 R |
| 3,949,388 | 4/1976 | Fuller ........................... 128/2.1 A X |

FOREIGN PATENT DOCUMENTS

| 171960 | 12/1965 | U.S.S.R. ........................ 128/2 S |
| 171961 | 12/1965 | U.S.S.R. ........................ 128/2 S |

OTHER PUBLICATIONS

Schuder, J.C. et al, "Energy Transport to a Coil Which Circumscribes a Ferrite Core and Is Implanted Within the Body", IEEE Transactions on Bio-Med. Engr., vol. BME-12, Nos. 3-4, Jul./Oct. 1965.
Mackay et al., "Endoradiosonde", Nature, Jun. 15, 1957 pp. 1239-1241.
Mackay, "Radio Telemetering from within the Human Body", IRE Trans on Med Elec., Jun. 1959 pp. 100-105.
Mackay, "Endoradiosondes: Further Notes", IRE Trans 1961 pp. 67-73.
Electronics for Naval Personnel, Dover Publ. N.Y. 1969 (NAVPERS 10087-B), pp. 217-218.
Roeber, F. W. et al, "An Intra-oral Electronic system for the Study of Dental Occlusion", Med & Biol. Engng, vol. 6 1968, pp. 677-679.
Watson, B. W. et al, "The Long-Recording of ICP", Phys. Med. Biol. Jan. 1974, vol. 19 #1 pp. 86-95.
Mollon, Jos. "Implantable Transducer for In-Vivo Measurement of Bone Strain", 1972 ISA Conference Publ. BM 72302 p. 7-14.

Primary Examiner—Robert W. Michell
Assistant Examiner—Francis J. Jaworski
Attorney, Agent, or Firm—Berman, Aisenberg & Platt

[57] ABSTRACT

A process for the measurement in vivo of the degree of bone consolidation, characterized in that it consists of implanting directly on the surface of the bone a transmitter with its power supply circuit, the oscillation frequency of the transmitter being capable of varying about a predetermined value during stresses applied to the bone to which the transmitter is secured. Signals emitted by the transmitter are received on a suitable external receiver positioned adjacent the transmitter. The receiver output signals are utilized for various purposes, such as checking, measurement and recording.

9 Claims, 7 Drawing Figures

PROCESS AND DEVICE FOR THE IN VIVO MEASUREMENT OF BONE CONSOLIDATION

BACKGROUND OF THE INVENTION

The present invention relates to the in vivo measurement of the degree of bone consoldiation.

The degree of bone consolidation can be assessed by measuring the rigidity of the bone callus formed. Measurements repeated at regular intervals over several months make it possible to determine when the bone becomes sufficiently rigid.

A known device for carrying out such measurments comprises a bridge of extensometric gauges disposed externally on the limb or part of the body within which lies the bone that is undergoing consolidation after a fracture or crack, the bridge is connected to the bone by two metal rods screwed into the bone.

An amplification and measurement circuit is connected to the bridge to effect the necessary measurements.

When known moments of flexion are applied to the bone, the gauge bridge detects any variations in stresses which can thus be measured.

The idea of implanting such gauges in vivo has also been considered but, owing to their considerable bulkiness it is necessary to provide an external power supply for the gauges.

It is an object of the present invention to palliate the drawbacks of these techniques by providing an extremely reliable process which results in only a minimum of discomfort for the patient.

SUMMARY OF THE INVENTION

The present invention provides a process for the measurement in vivo of the degree of bone consolidation, and it is characterized by implanting a transmitter with its power supply circuit directly onto the surface of the bone. The oscillation frequency of the transmitter is capable of varying about a predetermined value during stresses applied to the bone to which the transmitter is secured. The signals emitted by the transmitter are received on a suitable external receiver positioned adjacent the transmitter and the output signals of the receiver may be used for various purposes, such as checking, measurement and recording.

According to a particularly advantageous embodiment of the invention, the transmitter comprises a blocking oscillator using, as a transformer, a high permeability ferrite torus which is fastened by means of a suitable resin to an osteosynthesis plate screwed to the bone to be studied.

In order to effect more complete measurements, a telemeter transmitter can be associated with the receiver; and a telemetering receiver and a measurement amplifying recording device may also be associated with the receiver.

The ferrite torus comprises a winding which determines the frequency of the blocking oscillator. A slight stress transmitted to the torus results in a variation in its inductance, which may be as high as 50%. Owing to the use of a ferrite torus as a detector instead of stress gauges, and by making the oscillator circuits in the form of a printed coil, a transmitter may be provided which takes up very little space and which can be implanted directly onto the bone to be studied without requiring physical liaison with the outside of the patient's body.

Furthermore, owing to the very low rate of consumption of the transmitter, autonomous operation lasting considerably longer than 18 months may be obtained.

BRIEF DESCRIPTION OF THE DRAWINGS

Other characteristics and advantages will be brought out in the following detalied description of a preferred embodiment of the invention, this description being given purely by way of example and with respect to the appended drawings in which.

DESCRIPTION OF THE PREFERRED EMBODIMENT

Figure 1:
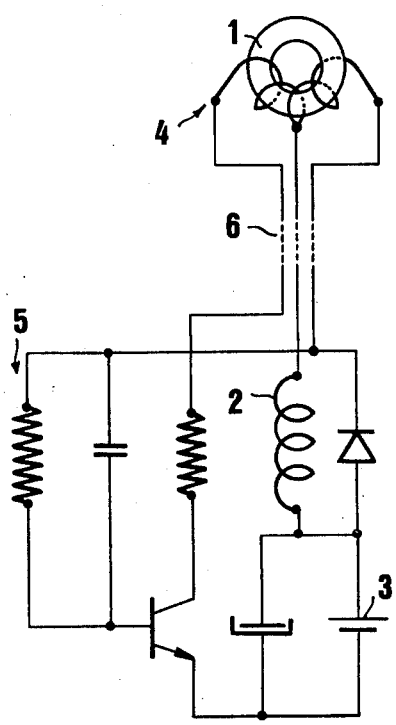
FIG. 1 is an electrical schematic diagram of a preferred embodiment of a transmitter according to the invention.

The transmitter of the present invention, for which an electrical diagram is shown in FIG. 1, comprises a blocking oscillator using a ferrite torus 1 as a transformer, having for example an outer diameter of 4 mm, comprising twice 50 hand wound turns. The relaxation frequency is situated around 1 kHz. The antenna consists of a printed spiral coil 2, comprising for example 40 turns of 25 mm external diameter. The components of the transmitter are preferably of the subminiature type (for hydrid circuits). Power is supplied to the transmitter by a 1.35 volt microbattery 3.

Figure 4:
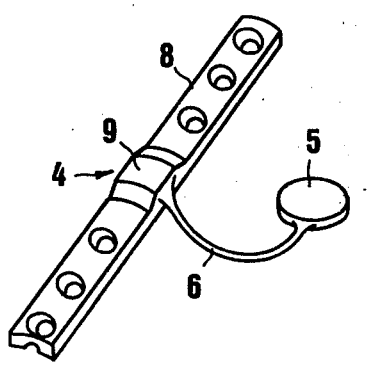
FIG. 4 illustrates the transmitter of the invention mounted on an osteosynthesis plate.
Figure 5:
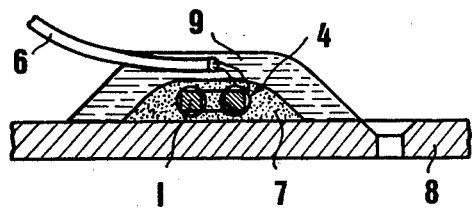
FIG. 5 is a diagrammatic cross section of the detector of the invention secured to the plate of FIG. 4.

In the mode of embodiment shown in FIGS. 1, 4 and 5, the transmitter is separated into two portions, one portion 4 consisting of the detector (torus 1) and the other portion 5 by the transmitter proper, these two portions preferably being connected by a Teflon coated cable 6 sheathed in a "Silastic" (Dow Corning Company) extra flexible tube.

The printed circuit of the transmitter is manufactured, for example, by photographic reduction, the coil constituting antenna 2 being designed by an analog computer. Transmitter 5 is vacuum moulded in an epoxide resin such as "medical araldite".

The ferrite torus 1 is preferably embedded (FIG. 5) in an epoxide resin 7, as shown in FIG. 5.

The detector 4 so constituted is integral with a prescoured osteosynthesis plate 8 adapted to be screwed to the bone to be studied facing the fracture or crack. The osteosynthesis plate 8 may be made of any suitable material well known in the art. See, for example, *Webster's Third New International Dictionary Unabridged* (1971) under "osteosynthesis" (p.1597); and *Larousse Médical* pages 463-464 (1975 edition), Imprimerie Hérissey, France. Detector 4 is encased in a special elastomer such as a silicone 9 (which may be that known as "Silastic" which is manufactured by the Dow Corning Company).

Figure 6:
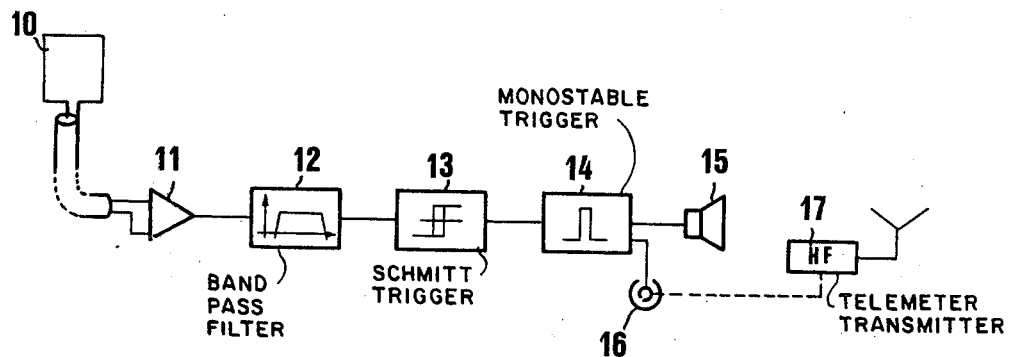
FIG. 6 is a block diagram of a receiver according to the present invention.

The receiver shown in FIG. 6 comprises a square loop antenna 10, a wide band amplifier 11, a band-pass filter 12, a Schmitt trigger 13, a monostable trigger circuit 14 the output of which is connected to a sound producing device 15 and an output 16 for recording on a magnetophone.

The receiver of FIG. 6 is preferably small, autonomous and can be carried on the patient.

It it is desired to effect telemetering, an HF telemeter transmitter 17 is associated with the receiver.

Figure 7:
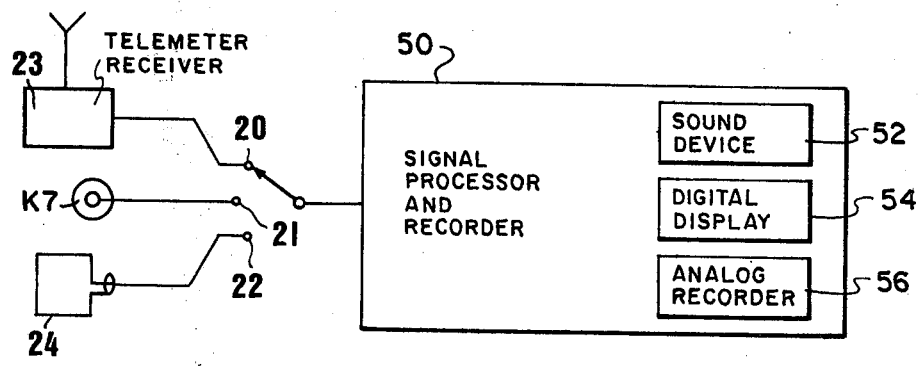
FIG. 7 is a block diagram of a signal processor and recorder 50 for utilizing the signals by the transmitter of the present invention.

FIG. 7 shows a signal processor and recorder 50 having three inputs: a radio telemetering input 20, a magnetophone input 21 and a direct input 22.

Input 20 is connected to the telemetering receiver 23 tuned to the telemetering transmitter 17 of the receiver of FIG. 6.

Input 21 is a magnetophone read-out input and input 22 is connected to a square loop antenna 24 similar to the square loop antenna 10 of the receiver of FIG. 6.

Inputs from 20, 21 or 22 may be processed through any suitable signal processor and recorder 50. Recorder 50 may include a sound output device 52, a digital display 54, and/or an analog signal recorder 56.

The detector 4 and emitter 5 integral with the osteosynthesis plate 8 are implanted on the fractured or cracked bone. After the operation, known forces and moments of flexion are applied to the limb in question once a week, for example.

Figure 2:
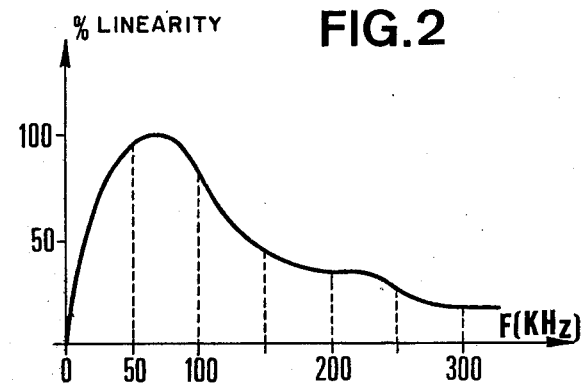
FIG. 2 is a graph of the spectrum radiated by the transmitter of FIG. 1.
Figure 3:
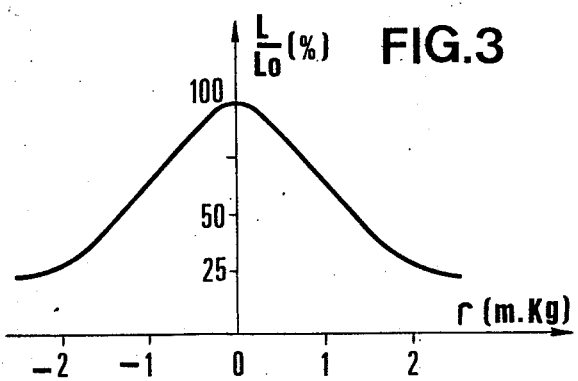
FIG. 3 is a graph which illustrates variations in the torus inductance of the transmitter of the present invention as a function of the applied moment.

Any slight stresses transmitted to torus 1 or the detector 4 result in variations in inductance which may be greater than 50% (FIG. 3). Such variations in inductance induce variations in the frequency of the oscillator of emitter 5. FIG. 2 illustrates the spectrum as a linear percent of maximum by a emitter having a power output of 3 $\mu$W and a range of 20 cm.

The probe (square shaped loop antenna 10 although one skilled in the art will understand that a circular loop may be used) of the receiver of FIG. 6 should be positioned at a maximum distance of 20 cm from the implantation site of the transmitter.

The receiver permits both auditive control by means of the sound device 15 and recording on an ordinary magnetophone. If coupled to the telemetering emitter 17 and worn by the patient, the receiver permits telemetering to be effected at a distance to monitor bone stress during walking, running, or the like.

The signal processor and recorder 50 of FIG. 7 permits sound control by device 26 at a distance, permits measurement of stress to be digitally displayed at 54 and has an analog output which may be connected to a recorder 56.

It should be emphasized that development over a period of time of measurements obtained after calibration determine the bone consolidation curve.

Input 21 of the signal processor and recorder 50 permits reuse of previous recordings. Input 22 permits direct use of the signal processor and recorder 50 without passing through the receiver of FIG. 6 by placing the square loop antenna 24 at maximum of 20 cm from the transmitter.

The very low power consumption of the transmitter (6 $\mu$W) provides real autonomy of considerably longer than 18 months. Its small size (diameter 30 mm, thickness 4 mm) enables it to be used without distress to the patient.

In the preferred embodiment of FIGS. 1, 4 and 5, the transmitter is made in two parts 4 and 5, but it is obviously possible to miniaturize the transmitter proper (5) even further to incorporate it in the detector 4 and secure it directly onto the osteosynthesis plate 8. It should further be noted that such a detector-transmitter can easily be adapted to measure parameters other than stresses (such as temperature, an electrocardiogram, or the like).

Finally, the invention is obviously not limited to the modes of embodiment shown and described above but covers all the variants.

We claim:

1. A process for detecting in vivo the degree of consolidation of a fractured bone, comprising the steps of:
   implanting a transmitter with its power supply, said transmitter comprising a blocking oscillator having as a transformer a high permeability ferrite torus implanted on the surface of said bone, the frequency of oscillation of said transmitter varying about a predetermined value in response to any stresses applied to said bone;
   applying a known force to said bone; and
   receiving the signals emitted by said transmitter.

2. The process as set forth in claim 1, wherein said implanting step includes the steps of:
   adhering said ferrite torus to an osteosythesis plate by means of a non-flow resin; and
   securing said plate to said bone.

3. The process as set forth in claim 2, wherein said receiving step includes the step of positioning an autonomous receiver adjacent the position where said transmitter is implanted.

4. The process as set forth in claim 3, further comprising the steps of providing said receiver with means for sounding a warning and means for recording the received signals on a magnetophone.

5. The process as set forth in claim 4, further comprising the steps of:
   transmitting the output of said receiver via a telemetering transmitter; and
   receiving the output of said telemetering transmitter on a remotely located telemetering receiver; and
   processing the signals received by said telemetering receiver on measurement and said recording control means.

6. Apparatus, which comprises:
   means for detecting and measuring in vivo the degree of consolidiation of a fractured bone comprising means for transmitting an oscillating signal whose frequency of oscillation varies about a predetermined value in response to stress applied to said bone; said transmitting means including a power supply and a blocking oscillator having a transformer for detecting the stress applied to said bone and comprising a high permeability ferrite torus;
   further comprising an osteosynthesis plate to which said ferrite torus is adhered, said plate adapted to be secured to said bone; and
   means positioned in the vicinity of said transmitting means for receiving said oscillating signal.

7. The apparatus as set forth in claim 6, wherein said receiving means includes means for sounding a warning and means for recording said oscillating signal on a magnetophone.

8. The apparatus as set forth in claim 7, further comprising:
   a telemetering transmitter for transmitting the output of said receiving means;

a remotely located telemetering receiver for receiving the signals transmitted by said telemetering transmitter; and measurement and recording control means for processing the signals received by said telemetering receiver.

9. The apparatus as set forth in claim 8, wherein said measurement and recording control means includes a sound device, a digital measurement display device and an analog output adapted to be connected to a recorder.

* * * * *